US012688932B2

(12) United States Patent
Beall et al.

(10) Patent No.: US 12,688,932 B2
(45) Date of Patent: Jul. 21, 2026

(54) OPTIMIZING NON-SEQUENTIAL PARSING OF INFORMATION EXTRACTED FROM MACHINE-READABLE CODES

(71) Applicant: O&M Halyard, Inc., Glen Allen, VA (US)

(72) Inventors: Michael Beall, Richmond, VA (US); Christopher Farmer, Augusta, SC (US); Ishrat Jahan, Cheektowaga, NY (US); Monsur Ahmed, Queens, NY (US)

(73) Assignee: O&M Halyard, Inc., Glen Allen, VA (US)

( * ) Notice: Subject to any disclaimer, the term of this patent is extended or adjusted under 35 U.S.C. 154(b) by 0 days.

(21) Appl. No.: 18/628,144

(22) Filed: Apr. 5, 2024

(65) Prior Publication Data

US 2024/0339208 A1      Oct. 10, 2024

Related U.S. Application Data

(60) Provisional application No. 63/494,555, filed on Apr. 6, 2023.

(51) Int. Cl.
*G16H 40/40*      (2018.01)
*G06K 7/14*       (2006.01)
*G06K 7/10*       (2006.01)

(52) U.S. Cl.
CPC ........... *G16H 40/40* (2018.01); *G06K 7/1417* (2013.01); *G06K 2007/10504* (2013.01)

(58) Field of Classification Search
CPC ................ G16H 40/40; G06K 7/1417; G06K 2007/10504; G06F 40/205; G06F 8/427
See application file for complete search history.

(56) References Cited

U.S. PATENT DOCUMENTS 11,520,827 B2    12/2022  Pamarthi et al.
2008/0098292 A1*  4/2008  Embry .................. G06F 40/174
                                                  715/224

(Continued)

FOREIGN PATENT DOCUMENTS

WO      WO-2020231590 A1 * 11/2020   ............. G16H 40/67

OTHER PUBLICATIONS

M. Wurzenberger, F. Skopik, R. Fiedler and W. Kastner, "Applying high-performance bioinformatics tools for outlier detection in log data," 2017 3rd IEEE International Conference on Cybernetics (CYBCONF), Exeter, UK, 2017, pp. 1-8, doi: 10.1109/CYBConf. 2017.7985760. (Year: 2017).*

(Continued)

*Primary Examiner* — Sun M Li
(74) *Attorney, Agent, or Firm* — Dority & Manning, P.A.

(57)      ABSTRACT

Object information is received via an application programming interface (API) from a requesting computing device. The object information is (a) extracted from a machine-readable code associated with the object, or (b) derived from information extracted from the machine-readable code associated with the object. A non-sequential parsing process is performed to the object information to identify one or more values for one or more fields of a plurality of unique fields. Performing the non-sequential parsing process includes applying a plurality of regular expressions to the object information to identify the one or more values. Each of the plurality of regular expressions is configured to identify values for at least one field of the plurality of unique fields. For each of the one or more values, a data object is that comprises the value and information indicative of the field for the value.

17 Claims, 4 Drawing Sheets

(56) References Cited

U.S. PATENT DOCUMENTS

| | | | |
|---|---|---|---|
| 2014/0040287 A1* | 2/2014 | Frome | G06F 16/252 |
| | | | 707/E17.058 |
| 2014/0279864 A1* | 9/2014 | Lopyrev | G06F 16/258 |
| | | | 707/755 |
| 2020/0005258 A1* | 1/2020 | Miller | G06F 40/174 |
| 2020/0226214 A1* | 7/2020 | Reddekopp | G06F 16/1734 |
| 2020/0394398 A1* | 12/2020 | Pamarthi | G06F 16/345 |
| 2021/0043291 A1* | 2/2021 | Kress-Spatz | G16H 40/67 |
| 2021/0043319 A1* | 2/2021 | Lequeux | G06F 16/2272 |
| 2022/0309335 A1* | 9/2022 | Varghese | G06N 3/092 |
| 2023/0046842 A1* | 2/2023 | Hauptman | G16H 40/20 |
| 2023/0325373 A1* | 10/2023 | Reese | G06V 30/413 |
| | | | 707/741 |
| 2025/0252252 A1* | 8/2025 | Shetty | G06K 7/1417 |

OTHER PUBLICATIONS

B. Di Martino, A. Posillipo, S. Nacchia and S. A. Maisto, "A Q&A Tool to Produce an Ad-Hoc OpenAPI Specification to Identify Equivalent REST Api Services," 2018 IEEE International Conference on Smart Computing (SMARTCOMP), Taormina, Italy, 2018, pp. 375-380, doi: 10.1109/SMARTCOMP.2018.00032. (Year: 2018).*

Gundersen S, Kalaš M, Abul O, Frigessi A, Hovig E, Sandve GK. Identifying elemental genomic track types and representing them uniformly. BMC Bioinformatics. Dec. 30, 2011;12:494. doi: 10.1186/1471-2105-12-494. PMID: 22208806; PMCID: PMC3315820. (Year: 2011).*

B. C. Brodie, D. E. Taylor and R. K. Cytron, "A Scalable Architecture For High-Throughput Regular-Expression Pattern Matching," 33rd International Symposium on Computer Architecture (ISCA'06), Boston, MA, USA, 2006, pp. 191-202, doi: 10.1109/ISCA.2006.7. (Year: 2006).*

R. D. Cameron et al., "Bitwise data parallelism in regular expression matching," 2014 23rd International Conference on Parallel Architecture and Compilation Techniques (PACT), Edmonton, AB, Canada, 2014, pp. 139-150, doi: 10.1145/2628071.2628079. (Year: 2014).*

International Search Report and Written Opinion for PCT/US2024/023337, dated Jun. 26, 2024, 11 pages.

* cited by examiner

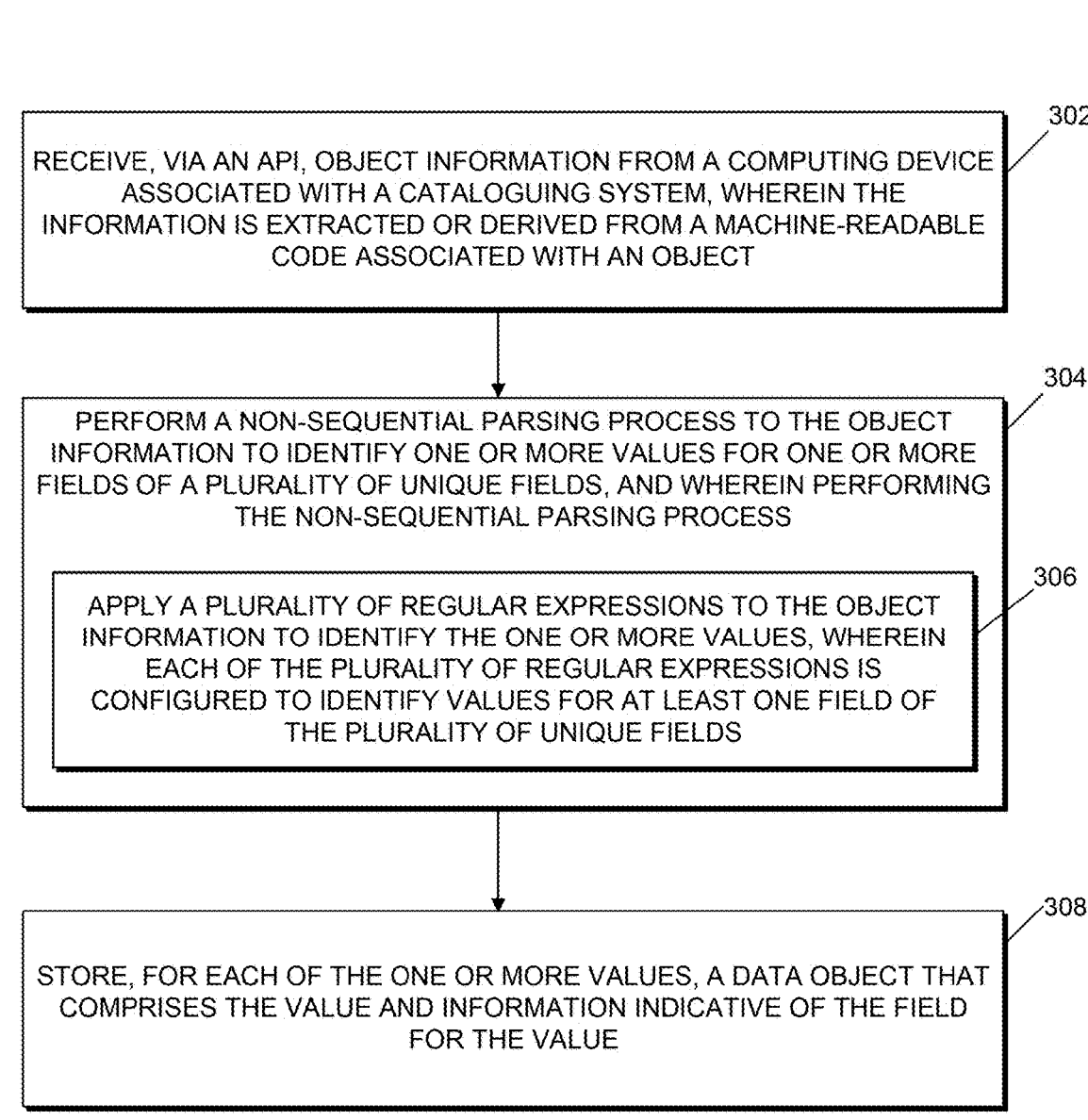

300

302

RECEIVE, VIA AN API, OBJECT INFORMATION FROM A COMPUTING DEVICE ASSOCIATED WITH A CATALOGUING SYSTEM, WHEREIN THE INFORMATION IS EXTRACTED OR DERIVED FROM A MACHINE-READABLE CODE ASSOCIATED WITH AN OBJECT

304

PERFORM A NON-SEQUENTIAL PARSING PROCESS TO THE OBJECT INFORMATION TO IDENTIFY ONE OR MORE VALUES FOR ONE OR MORE FIELDS OF A PLURALITY OF UNIQUE FIELDS, AND WHEREIN PERFORMING THE NON-SEQUENTIAL PARSING PROCESS

306

APPLY A PLURALITY OF REGULAR EXPRESSIONS TO THE OBJECT INFORMATION TO IDENTIFY THE ONE OR MORE VALUES, WHEREIN EACH OF THE PLURALITY OF REGULAR EXPRESSIONS IS CONFIGURED TO IDENTIFY VALUES FOR AT LEAST ONE FIELD OF THE PLURALITY OF UNIQUE FIELDS

308

STORE, FOR EACH OF THE ONE OR MORE VALUES, A DATA OBJECT THAT COMPRISES THE VALUE AND INFORMATION INDICATIVE OF THE FIELD FOR THE VALUE

Figure 3

OPTIMIZING NON-SEQUENTIAL PARSING OF INFORMATION EXTRACTED FROM MACHINE-READABLE CODES

PRIORITY CLAIM

The present application claims priority to, and the benefit of, U.S. Provisional Patent Application No. 63/494,555, having a filing date of Apr. 6, 2023. Applicant incorporates the application herein by reference in its entirety.

FIELD

The present disclosure relates generally to parsing of encoded information. More particularly, the present disclosure relates to optimizations to non-sequential parsing of information that is extracted from machine-readable codes.

BACKGROUND

Machine-readable codes are created by encoding information within a visual representation. These encodings exist in a variety of different formats (e.g., barcodes, QR codes, proprietary visual encodings, etc.). When generating a machine-readable code, information is generally encoded in a certain order. Often, when designing cataloguing systems, machine-readable codes will be formatted to encode information in a standardized and sequential order so that the encoded information is easily parsed once extracted from the machine-readable code. For example, a machine-readable code such as a barcode may be formatted so that the encoded information sequentially includes an object identifier, a serial number, and a lot number.

SUMMARY

Aspects and advantages of embodiments of the present disclosure will be set forth in part in the following description, or can be learned from the description, or can be learned through practice of the embodiments.

One example aspect of the present disclosure is directed to a computing system. The computing system includes one or more processors and one or more non-transitory computer-readable media that store instructions that, when executed by the one or more processors, cause the one or more processors to perform operations. The operations include receiving, via an application programming interface (API), object information from a requesting computing device, wherein the object information is (a) extracted from a machine-readable code associated with the object; or (b) derived from information extracted from the machine-readable code associated with the object. The operations include performing a non-sequential parsing process to the object information to identify one or more values for one or more fields of a plurality of unique fields, and wherein performing the non-sequential parsing process includes applying a plurality of regular expressions to the object information to identify the one or more values, wherein each of the plurality of regular expressions is configured to identify values for at least one field of the plurality of unique fields. The operations include storing, for each of the one or more values, a data object that comprises the value and information indicative of the field for the value.

Another example aspect of the present disclosure is directed to a computer-implemented method. The method includes receiving, by a computing system comprising one or more processor devices via an API, object information from a requesting computing device, wherein the object information is (a) extracted from a machine-readable code associated with the object; or (b) derived from information extracted from the machine-readable code associated with the object. The method includes performing, by the computing system, a non-sequential parsing process to the object information to identify one or more values for one or more fields of a plurality of unique fields, and wherein performing the non-sequential parsing process includes applying, by the computing system, a plurality of regular expressions to the object information to identify the one or more values, wherein each of the plurality of regular expressions is configured to identify values for at least one field of the plurality of unique fields. The method includes storing, by the computing system for each of the one or more values, a data object that comprises the value and information indicative of the field for the value.

Another example aspect of the present disclosure is directed to one or more non-transitory computer-readable media that store instructions that, when executed by one or more processors of a computing system, cause the one or more processors to perform operations. The operations include receiving, via an API, object information from a requesting computing device, wherein the object information is (a) extracted from a machine-readable code associated with the object; or (b) derived from information extracted from the machine-readable code associated with the object. The operations include performing a non-sequential parsing process to the object information to identify one or more values for one or more fields of a plurality of unique fields, and wherein performing the non-sequential parsing process includes applying a plurality of regular expressions to the object information to identify the one or more values, wherein each of the plurality of regular expressions is configured to identify values for at least one field of the plurality of unique fields. The operations include storing, for each of the one or more values, a data object that comprises the value and information indicative of the field for the value.

Other aspects of the present disclosure are directed to various systems, apparatuses, non-transitory computer-readable media, user interfaces, and electronic devices.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

Detailed discussion of embodiments directed to one of ordinary skill in the art is set forth in the specification, which makes reference to the appended figures, in which:

FIG. 3 depicts a flow chart diagram of an example method to perform non-sequential parsing of object information for extraction of values according to example embodiments of the present disclosure.

Figure 1:
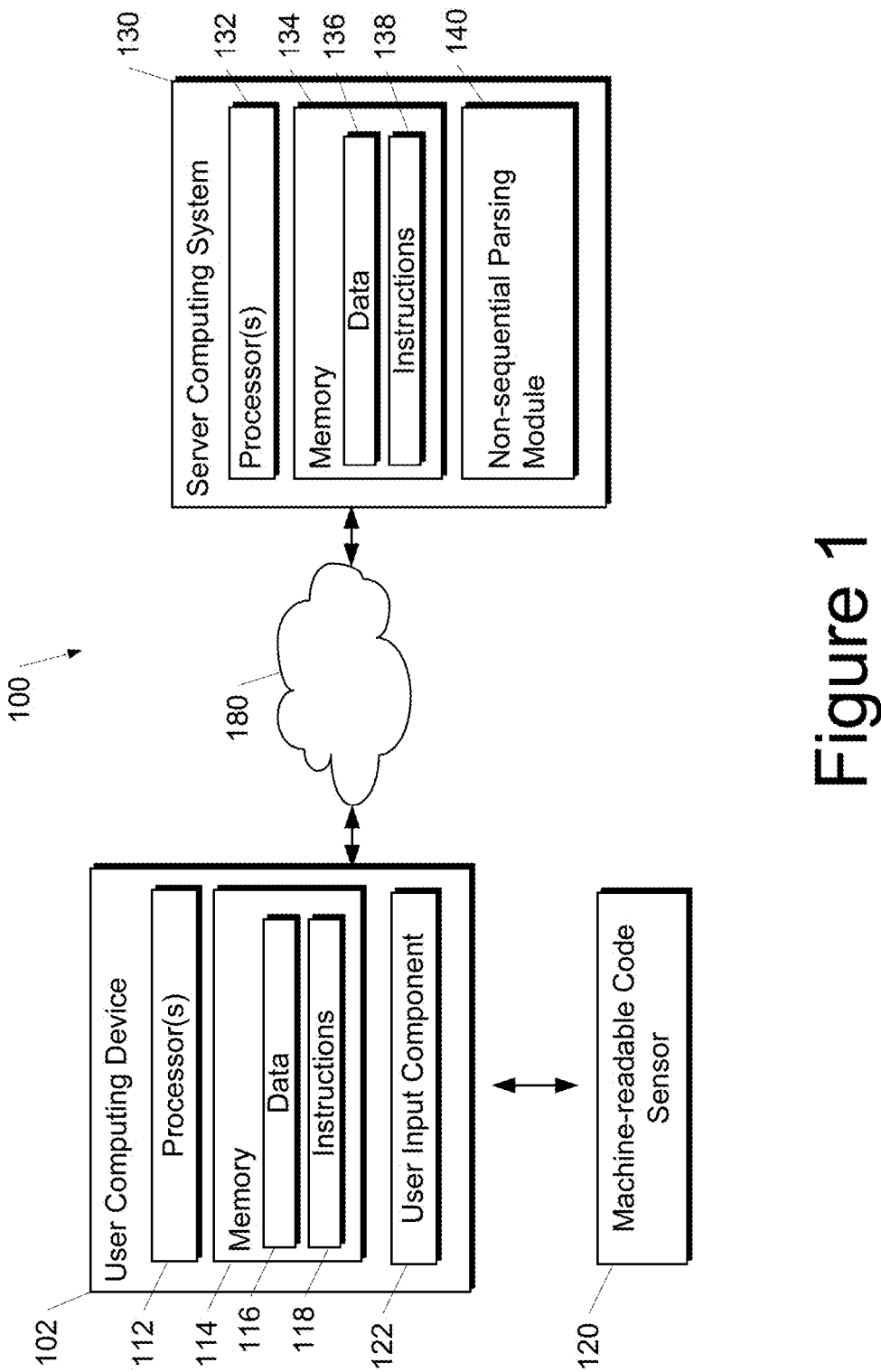
FIG. 1 depicts a block diagram of an example computing system that performs non-sequential parsing of encoded information according to example embodiments of the present disclosure.

Reference numerals that are repeated across plural figures are intended to identify the same features in various implementations.

DETAILED DESCRIPTION

Overview

Generally, the present disclosure is directed to parsing of encoded information. More particularly, the present disclosure relates to optimizations to non-sequential parsing of information that is extracted from machine-readable codes. For example, as described previously, machine-readable codes are created by encoding information within a visual representation. Often, machine-readable codes are formatted to encode information in a standardized and sequential order so that the encoded information is easily parsed once extracted from the machine-readable code. However, the increasing interconnectedness of cataloguing systems has led to the occurrence of scenarios in which a system must extract encoded information from a machine-readable code without knowledge of how the encoded information is formatted.

As an example, assume that a first system (e.g., a laboratory that creates medical compounds, a medical supply manufacturer that supplies surgical equipment, etc.) utilizes a format for information encoded within a machine-readable code that sequentially encodes values for a product identifier field, a serial number field, and a lot number field. A second system (e.g., a hospital) that does not utilize or recognize serial number fields can receive the machine-readable code and extract the encoded information within it. As the second system does not utilize a serial number field, the second system may be unable to determine where information associated with the serial number field ends and where information associated with the lot number field begins, therefore stopping the parsing process before values for the lot number field can be parsed.

Accordingly, implementations of the present disclosure propose optimizations for non-sequential parsing of information extracted from machine-readable codes. More specifically, a computing system (e.g., a system providing parsing services or microservices, etc.) can obtain object information via an Application Programming Interface (API) from a computing device associated with a cataloguing system (e.g., an inventory management system, etc.). The object information can be extracted from a machine-readable code associated with the object, or may be derived from information extracted from the machine-readable code.

For example, the computing system can be a computing system for provision of barcode parsing services within a medical cataloguing system, the object can be a medical device, and the machine-readable code can be a barcode located on a surface of the medical device (e.g., a GS1-standardized barcode, a two-dimensional barcode (e.g., a QR code, etc.), a Health Industry Bar Code (HIBC), etc.). The computing device can receive the object information from a scan of the barcode with a communicatively coupled barcode scanning device, and can transmit the object information to the computing system.

The computing system can perform a non-sequential parsing process to the object information to identify one or more values for one or more fields of a plurality of unique fields. To perform the non-sequential parsing process, the computing system can apply a plurality of regular expressions to the object information to identify the one or more values. Each of the plurality of regular expressions can be configured to identify values for at least one of the plurality of unique fields. Once identified, each of the value(s) can be stored in a data object that includes the value and information identifying the field for the value.

To follow the previous example, the first computing system (e.g., the laboratory system, a medical supply manufacturer that supplies surgical equipment, etc.) that utilizes the format for machine-readable codes in which the product identifier field, the serial number field, and the lot number field are sequentially encoded can provide the machine-readable code to the second computing system (e.g., the hospital system, etc.). As described previously, the second computing system does not recognize the information associated with the serial number field. However, the computing system can apply a first regular expression that is configured to identify values for a product identifier field to extract the value for the product identifier field from the encoded information. The computing system can then apply a second regular expression configured to identify values for a lot number field to extract the value for the lot number field from the encoded information. In such fashion, implementations of the present disclosure can parse values from encoded information in a non-sequential manner, allowing for extraction of values from encoded information that includes values for unknown fields.

Aspects of the present disclosure provide a number of technical effects and benefits. For example, as described previously, encoding of information using different formats can serve as a vector for substantial errors and inefficiencies when communicating machine-readable codes between computing systems. In turn, these inefficiencies can necessitate that the encoded information be manually entered by a human, leading to the expenditure of substantial resources associated with manual data entry (e.g., compute cycles, energy, memory, power, storage, bandwidth, etc.). However, with the large quantity of systems within interconnected networks, enforcing one standard format for all machine-readable codes is not feasible. Accordingly, implementations of the present disclosure provide the capability to parse values from encoded information in a non-sequential fashion, therefore reducing, or eliminating, the aforementioned inefficiencies.

With reference now to the Figures, example embodiments of the present disclosure will be discussed in further detail.

Example Devices and Systems

FIG. 1 depicts a block diagram of an example computing system 100 that performs non-sequential parsing of encoded information according to example embodiments of the present disclosure. The system 100 includes a user computing device 102, a server computing system 130, and a training computing system 150 that are communicatively coupled over a network 180.

The user computing device 102 can be any type of computing device, such as, for example, a personal computing device (e.g., laptop or desktop), a mobile computing device (e.g., smartphone or tablet), a gaming console or controller, a wearable computing device, an embedded computing device, or any other type of computing device.

The user computing device 102 includes one or more processors 112 and a memory 114. The one or more processors 112 can be any suitable processing device (e.g., a processor core, a microprocessor, an ASIC, an FPGA, a controller, a microcontroller, etc.) and can be one processor or a plurality of processors that are operatively connected. The memory 114 can include one or more non-transitory computer-readable storage media, such as RAM, ROM, EEPROM, EPROM, flash memory devices, magnetic disks, etc., and combinations thereof. The memory 114 can store data 116 and instructions 118 which are executed by the processor 112 to cause the user computing device 102 to perform operations.

The user computing device 102 can also include one or more user input components 122 that receives user input. For example, the user input component 122 can be a touch-sensitive component (e.g., a touch-sensitive display screen or a touch pad) that is sensitive to the touch of a user input object (e.g., a finger or a stylus). The touch-sensitive component can serve to implement a virtual keyboard. Other example user input components include a microphone, a traditional keyboard, or other means by which a user can provide user input.

The user computing device can include, or can be communicatively coupled to, a machine-readable code sensor 120. The machine-readable code sensor 120 can be any type, manner, and/or combination of sensor(s) sufficient to extract encoded information from a machine-readable code. For example, the machine-readable code sensor 120 may be a camera sensor that can capture an image of the machine-readable code, where the machine-readable code sensor 120 (and/or the user computing device 102) can extract encoded information from the image by performing image processing technique(s). For another example, the machine-readable code sensor 120 can be a light-emitting device that evaluates a degree of light reflected from portions of a machine-readable code to extract the encoded information from the machine-readable code.

The user computing device 102 can utilize the machine-readable code sensor 120 to extract encoded information from a machine-readable code for transmission to the server computing system 130. The server computing system 130 can parse the encoded information with a non-sequential parsing module 140. In some implementations, the user computing device 102 can provide the same encoded information to the server computing system 130 as was extracted from the machine-readable code. For example, if the machine-readable code is a barcode that encodes a string of binary values, the user computing device 102 may directly signal the string of binary values to the server computing system 130 (e.g., via an application programming interface (API) using network(s) 180). For example, the machine-readable code may be a barcode that encodes a string of binary values in two dimensions (e.g., a QR code, etc.). For another example, the machine-readable code may store information in accordance with some information encoding standard, such as an HIBC standard or GS1 standard.

Alternatively, in some implementations, the user computing device 102 can provide information derived from the machine-readable code to the server computing system. To follow the previous example, rather than provide the string of binary values to the server computing system, the machine-readable code sensor 120 may convert the string of binary values to a more interpretable format (e.g., hexadecimal values, alphanumeric characters, etc.). Detection and transmission of encoded information will be discussed in greater detail with regards to FIG. 2.

The server computing system 130 includes one or more processors 132 and a memory 134. The one or more processors 132 can be any suitable processing device (e.g., a processor core, a microprocessor, an ASIC, an FPGA, a controller, a microcontroller, etc.) and can be one processor or a plurality of processors that are operatively connected. The memory 134 can include one or more non-transitory computer-readable storage media, such as RAM, ROM, EEPROM, EPROM, flash memory devices, magnetic disks, etc., and combinations thereof. The memory 134 can store data 136 and instructions 138 which are executed by the processor 132 to cause the server computing system 130 to perform operations.

As described previously, the server computing system 130 can include a non-sequential parsing module 140. The non-sequential parsing module 140 can be software and/or hardware that can perform a non-sequential parsing process to parse values from encoded information. For example, the non-sequential parsing module can include a number of regular expressions that are each configured to identify values for certain fields. The server computing system 130 can receive encoded information from the user computing device 102. The non-sequential parsing module 140 can apply the regular expressions to the encoded information to extract values for respective fields.

In some implementations, the server computing system 130 includes or is otherwise implemented by one or more server computing devices. In instances in which the server computing system 130 includes plural server computing devices, such server computing devices can operate according to sequential computing architectures, parallel computing architectures, or some combination thereof.

The network 180 can be any type of communications network, such as a local area network (e.g., intranet), wide area network (e.g., Internet), or some combination thereof and can include any number of wired or wireless links. In general, communication over the network 180 can be carried via any type of wired and/or wireless connection, using a wide variety of communication protocols (e.g., TCP/IP, HTTP, SMTP, FTP), encodings or formats (e.g., HTML, XML), and/or protection schemes (e.g., VPN, secure HTTP, SSL).

Various components described herein can be implemented as cloud-based components. More specifically, components may be, or otherwise include, virtualized hardware and/or software resources. Alternatively, components may implement cloud-based services accessible by other computing devices via API(s). For example, the server computing system 130 can implement cloud-based databases that store information, such as medical information (e.g., associations between medical devices and encoded information, etc.). Access to services provided by the server computing system 130 can be mediated by an API. For example, the user computing device 102 may utilize machine-readable code sensor 120 to extract encoded information from a machine-readable code. The user computing device 102 can provide the encoded information to the server computing system 130 via an API for processing of the encoded information by a cloud-based information processing service implemented by the server computing system 130.

More generally, various aspects of the present disclosure can be implemented as services (e.g., microservices, etc.) in a cloud-based manner. For example, to implement a cloud-based parsing service for encoded information extracted from machine-readable codes, the server computing system may store data objects that include values extracted from encoded information within a cloud-based database accessible via APIs.

Figure 2A:
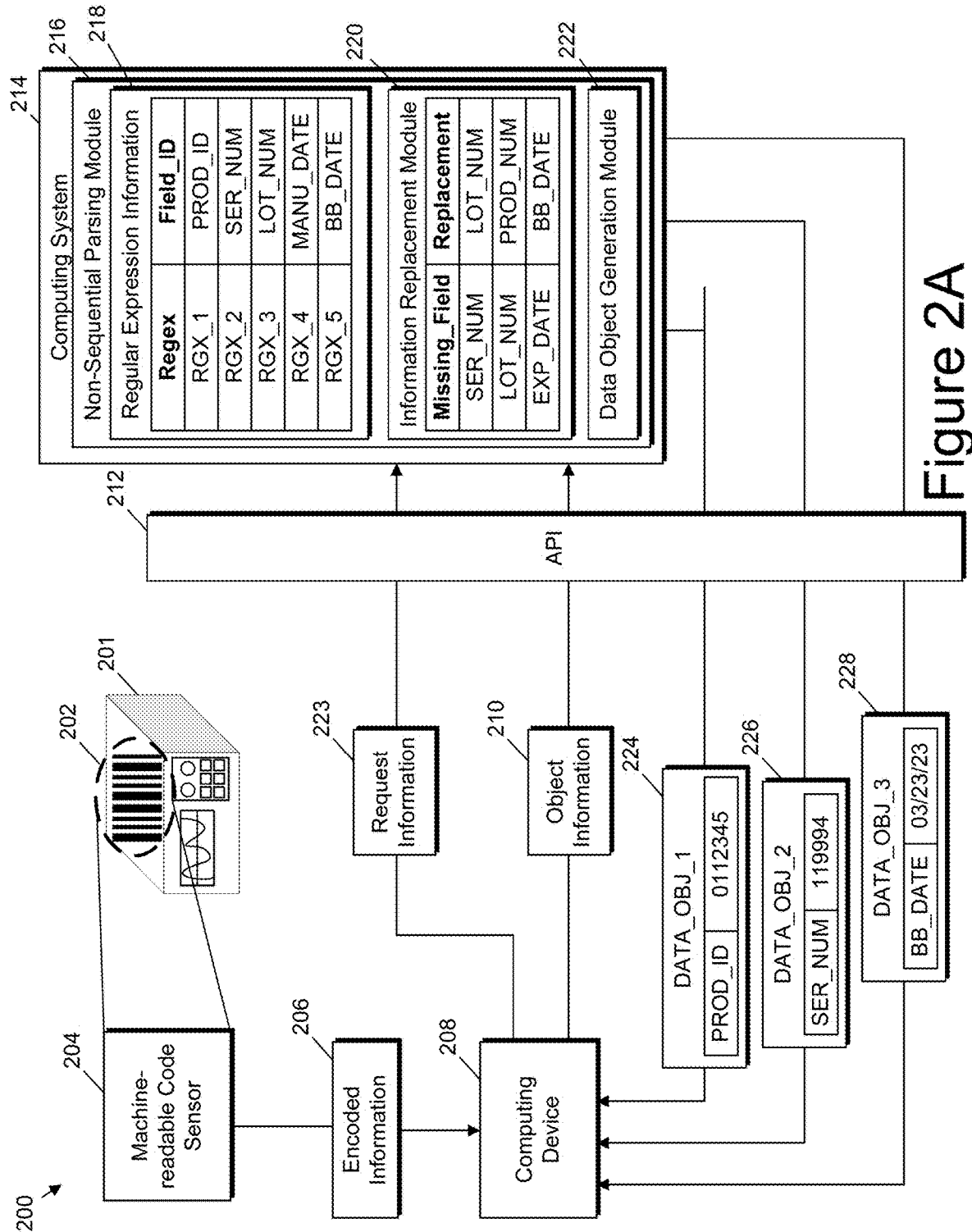
FIG. 2A is an overview data flow diagram 200 for non-sequential parsing of encoded information according to some implementations of the present disclosure.

FIG. 2A is an overview data flow diagram 200 for non-sequential parsing of encoded information according to some implementations of the present disclosure. Specifically, a computing device (e.g., user computing device 102 of FIG. 1, a desktop computing device, a laptop, a smartphone, etc.) can include, or can be communicatively coupled to, a machine-readable code sensor 204 (e.g., the machine-readable code sensor 120 of FIG. 1). The machine-readable code sensor 204 can extract encoded information 206 from a machine-readable code 202 that is located on the surface of an object 201. The computing device 208 communicatively coupled to the machine-readable code sensor 204 can receive the encoded information 206.

The computing device 208 can provide object information 210 to the computing system 214 via an API 212. The API 212 can be, or otherwise utilize, any type or manner of conventional API or API techniques. For example, the API can be an asynchronous RESTful API. In some implementations, the object information 210 can be the encoded information 206. Alternatively, in some implementations, the object information 210 can be information derived from the encoded information 206. For example, if the encoded information 206 is a string of binary values, the object information may be a string of alphanumeric characters derived from the string of binary values.

The computing system can receive the object information 210 from the computing device 208 via the API. The computing system can parse values from the object information 210 using the non-sequential parsing module 216. For example, the non-sequential parsing module 216 can include regular expression information 218. The regular expression information 218 can store a plurality of regular expressions. The regular expression information 218 can also map each of the plurality of regular expressions to a corresponding field ID of the field that the regular expression is configured to identify. To follow the depicted example, the regular expression RGX_1 may be configured to identify values for a PROD_ID (i.e., product ID) field. For another example, the regular expression RGX_2 may be configured to identify values for a SER_NUM (i.e., serial number) field.

A regular expression, also known as regex or regexp, is a sequence of characters that define a search pattern. A regular expression essentially consists of a combination of characters and metacharacters that collectively define a pattern. Regular expressions can match specific characters or character groups within a larger body of characters, and can be used to search for specific sequences of characters.

It should be noted that, throughout the specification, the term "encoded information" may be used to refer to "object information", such as object information 210, or used to refer to information included with the object information. Encoded information refers to the information extracted from the machine-readable code 202 prior to parsing by the computing system 214. As such, if a machine-readable code encodes a binary string, which in turn encodes an alphanumeric string, which in turn encodes values and corresponding field identifiers, encoded information may be used to refer to the binary string and/or the alphanumeric string.

Object information, on the other hand, refers to information sent by the computing device 208 to the computing system 214 regarding the object 201. As the machine-readable code 202 is located on a surface of the object 201, any encoded information 206 extracted from the machine-readable code 202 can be considered object information. Additionally, any information derived from the encoded information 206 can be considered object information. Further, the computing device 208 may provide supplemental information regarding the object 201, or state information or environmental information, within the object information 210. For example, the object information 210 may preliminarily indicate a type of object 201. For another example, the object information 210 may indicate a time and date at which the machine-readable code sensor 204 extracted the encoded information 206 from the machine-readable code 202. For yet another example, the object information can include the request information 223. In some implementations, the object information 210 may indicate alternative fields for the information replacement module 220. For example, the object information 210 may indicate that if a serial number value does not exist in the object information, to instead return a value for a product number field, or a lot number field, or a current date, in that order.

The non-sequential parsing module 216 can apply the regular expressions from the regular expression information 218 to the object information 210 to extract values for particular fields in a non-sequential manner. The fields for which values are extracted can be pre-defined fields recognized by the computing system 214. For example, assume that the computing system 214 is part of a network for managing inventory within a healthcare system, and the computing device 208 is a device associated with a cataloguing system for a medical device manufacturer. As a manufacturer, the cataloguing system may encode information for a "best by" date field, but refrain from encoding information for an expiration date field. Conversely, the computing system 214 for the healthcare system may store information for an expiration date field, but may lack a pre-determined field for a "best by" date.

It should be noted that, as described herein, a "non-sequential" parsing process (e.g., a process performed by the non-sequential parsing module 216) generally refers to a parsing process that is agnostic to a known sequence in which information is encoded. More specifically, a sequential parsing process would rely on knowledge of a particular information encoding sequence to parse information (e.g., the product ID field is always the first value encoded, the serial number field is always the second value encoded, etc.). Conversely, a non-sequential parsing process can recognize patterns within information that correspond to particular values, and, in some implementations, combinations of values and corresponding field identifiers, regardless of their position within the information. As a particular example, if a sequential parsing process expects a product ID value to be the first 4 values in a string of alphanumeric characters (e.g., encoded information), and a 6-digit manufacturing date value is instead the first value encoded, the sequential parsing process will be unable to parse the value (or any other value). Conversely, a non-sequential parsing process may not necessarily parse the manufacturing date value first, but will eventually parse the manufacturing date value as long as the process includes a regular expression configured to identify values for manufacturing date fields.

In some implementations, the fields are identified by a series of standardized field identifiers. For example, each of the values encoded in the object information 210 can be values for field(s) of a plurality of possible fields. The plurality of possible fields can be defined and standardized by a standards organization. For example, a standards organization may define "022" as being the field identifier for a product ID. In this manner, fields that are not utilized by the computing system 214 can still be identified by the computing system 214. To follow the previous example, even though the computing system 214 does not store values for a "best by" field, the regular expression information 218 can include a regular expression configured to identify values for "best by" fields so that the values for the "best by" fields can be utilized to replace missing information for other desired fields.

More specifically, the computing system can include an information replacement module 220. If the object information 210 does not include a value for a desired field, the information replacement module 220 can replace the missing value with a value from a field similar to the desired field. To follow the previous example, after application of the regular expression information 218 to the object information 210, the information replacement module 220 can determine that a value for a "best by" date field is included in the object information 210 but that a value for an expiration date field is not included in the object information 210. The information replacement module 220 can determine to assign the "best by" date's value to the expiration date field. In such fashion, the information replacement module 220 can ensure that information is extracted optimally from the object information 210 by minimizing inefficiencies that can arise from communicating systems utilizing similar but different field identifiers (e.g., serial number vs lot number, best-by date vs expiration date, etc.).

In some implementations, the computing device 208 can provide request information to the computing system 214 via the API 212. The request information 223 can indicate a request for values for particular fields. For example, the request information 223 can indicate a request for values for the product ID field, the serial number field, and the "best-by" date field. In some implementations, the request information can be included in the object information 210, or can otherwise be provided to the computing system 214 concurrently or near-concurrently with the object information 210.

The computing system 214 can generate data objects 224, 226, and 228 using data object generation module 222. The data objects 224-228 can be any type or manner of data object sufficient to convey information indicative of extracted values and associated field identifiers. In some implementations, the data objects 224-228 can be Javascript Object Notation (JSON) objects that each include a value and information indicative of the field for the value. For example, the data object 226 can include the value "Mar. 23, 2023" and the corresponding field identifier for the "best by" date field.

Figure 2B:
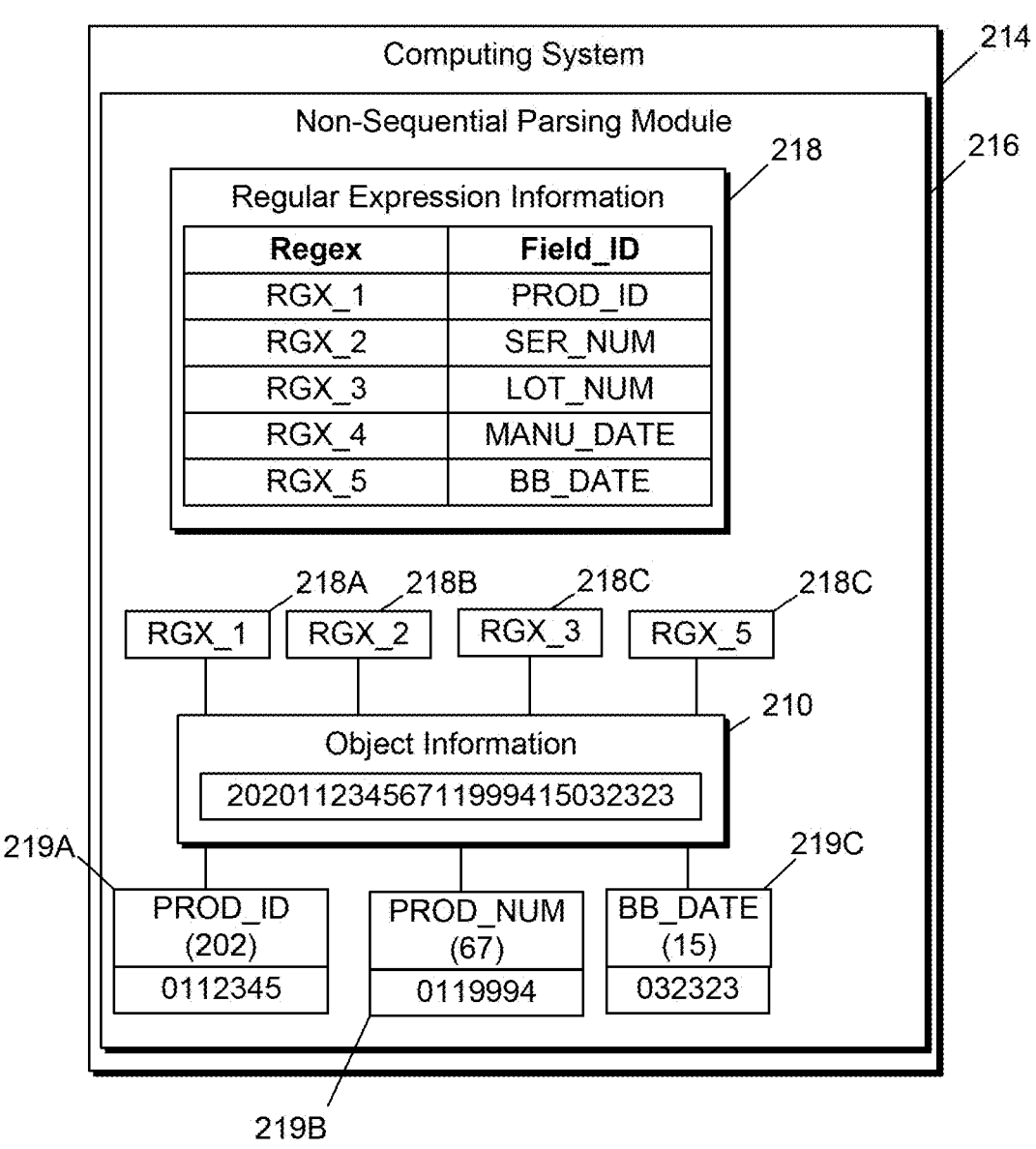
FIG. 2B is a data flow diagram for application of regular expressions to object information to extract values according to some implementations of the present disclosure.

For a specific example, turning to FIG. 2B, FIG. 2B is a data flow diagram for application of regular expressions to object information to extract values according to some implementations of the present disclosure. The computing system 214 can include the non-sequential parsing module 216. The non-sequential parsing module 216 can include the regular expression information 218. As described previously, the computing system 214 can obtain object information 210. The depicted object information 210 can include a sequence of numerical characters. Portions of the numerical characters can include (a) a value for a field and (b) an identifier for the field.

To follow the depicted example, assume that the request information 223 indicates a request for values for a Product ID field, a serial number field, and a "best-by" date field. The computing system 214 can select regular expressions to extract values for those particular fields. Specifically, the regular expression 218A can be configured to identify values for a PROD_ID (product ID) field. For example, the regular expression 218A can be configured to identify a pattern in which an 11-digit value starts with "01" and is preceded by the identifier (202). Here, (202) can be a pre-determined identifier for the product ID field, and product ID values can have a standardized length of 5 digits and can begin with a standardized prefix of (01). As this pre-determined patterned information is present in the object information 210, the regular expression 218A can be used to extract the value 219A (0112345) from the object information 210.

The computing system can select the regular expression 218B to extract a value for the serial number field. The regular expression 218B can be configured to identify a pattern that is not present in the object information 210. For example, the regular expression 218B can be configured to identify a value for a serial number field. Serial number fields can be standardized (e.g., by a standards organization) to begin with the identifier (9993) followed by a 7-digit value. As this pattern is not included in the object information 210, utilization of the regular expression 218B will not extract a value from the object information 210.

Because a value for the serial number field does not exist in the object information 210, the computing system 214 can determine to select a field similar to the serial number field using the information replacement module 220. The computing system can apply the regular expression configured to identify values for the similar field. For example, the non-sequential parsing module 216 can apply regular expression 218C, which is configured to identify values for the lot number field. The lot number field can be standardized to begin with the identifier (671) followed by a 5-digit value (e.g., 19994). Because the pre-determined patterned information exists in the object information 210, the value 219B for the lot number field can be extracted.

For another example, regular expression 218C can be configured to identify values for a BB_DATE ("best-by" date). "Best-by" date fields can be standardized (e.g., by a standards organization) to begin with the identifier (15) followed by a 6-digit value. As this pattern is included in the object information 210, the regular expression 218C can be utilized to extract the value 219C (e.g., "Mar. 23, 2023") from the object information 210 for the "best-by" field.

Returning to FIG. 2A, the data object generation module 222 can provide data object 224, 226, and 228 to the computing device 208 via the API 212. As described previously, in some implementations, the data objects 224-228 provided to the computing device 208 can be objects that include values for fields requested via the request information 223. Alternatively, in some implementations, the computing system can provide data objects with values for any fields identified in the object information 210.

Example Methods

FIG. 3 depicts a flow chart diagram of an example method 300 to perform non-sequential parsing of object information for extraction of values according to example embodiments of the present disclosure. Although FIG. 3 depicts steps performed in a particular order for purposes of illustration and discussion, the methods of the present disclosure are not limited to the particularly illustrated order or arrangement. The various steps of the method 300 can be omitted, rearranged, combined, and/or adapted in various ways without deviating from the scope of the present disclosure.

At 302, a computing system can receive, via an API, object information from a computing device associated with a cataloguing system. The object information is either (a) extracted from a machine-readable code associated with the object, or (b) derived from information extracted from the machine-readable code associated with the object. In some implementations, the machine-readable code can include a barcode. For example, the machine-readable code can be a barcode generated according to GS1 standards. For another example, the machine-readable code can be a barcode generated to HIBC standards (i.e., an HIBC barcode). Additionally, or alternatively, in some implementations, the machine-readable code can include a two-dimensional barcode that encodes information in two dimensions (e.g., vertically and horizontally, etc.). For example, the machine-readable code can be or include a QR code.

In some implementations, receiving the object information from the computing device associated with the cataloguing system can include receiving, via the API, an encoded sequence of values that is extracted from the machine-readable code associated with the object.

In some implementations, the object includes a medical resource or medical device, and the cataloguing system comprises a medical cataloguing system. Medical resources, and/or medical devices, can generally refer to any type or manner of device, resource, object, etc. For example, in some implementations, a medical device can refer to a device specifically designed for medical use (e.g., scalpels, surgical tools, scanning devices, syringes, dressings, scrubs or other manner of medical clothing, Personal Protective Equipment (PPE), etc.).

Additionally, in some implementations, medical devices, or medical resources, can refer to objects that are not specifically designed for medical use but may still be utilized in a medical facility (e.g., doctors office, hospital, outpatient center, clinic, etc.) or facilities that provide medical-adjacent services (e.g., a hospital accounting department, a hospital executives office, etc.). For example, medical resources can include devices or objects not specifically designed for medical use but may be utilized in a medical context (e.g., Virtual Reality (VR)/Augmented Reality (AR) devices, pagers, smartphones, laptops, compute resources, software licenses, etc.). For another example, medical resources can include devices or objects that can be utilized to facilitate provision of medical services, or to facilitate backend services for medical providers (e.g., pens, paper, paint, office furniture, staplers, pens, etc.).

Additionally, in some implementations, a medical resource can refer to expendable resources utilized within a medical context (e.g., blood or blood products, medicine, disposable medical wearables (e.g., PPE, scrubs, etc.), one-time use devices (e.g., scalpels, syringes, etc.), saline, food, etc.).

In some implementations, receiving the object information from the computing device associated with the cataloguing system includes receiving, from the computing device associated with the cataloguing system via the API, a sequence of binary values extracted from the machine-readable code associated with the object, and deriving the object information from the sequence of binary values.

At 304, the computing system can perform a non-sequential parsing process to the object information to identify one or more values for one or more fields of a plurality of unique fields. To perform the non-sequential parsing process, the computing system can, at 306, apply a plurality of regular expressions to the object information to identify the one or more values. Each of the plurality of regular expressions is configured to identify values for at least one field of the plurality of unique fields.

In some implementations, applying the plurality of regular expressions to the object information can include applying a first regular expression to the encoded sequence of values to identify a first value of a first field from a first segment of the encoded sequence of values. The first regular expression is configured to identify values for the first field.

Applying the plurality of regular expressions to the object information can further include applying a second regular expression to the encoded sequence of values to identify a second value of a second field from a second segment of the encoded sequence of values. The second regular expression is configured to identify values for the second field, and the second segment occurs prior to the first segment within the encoded sequence of values.

In some implementations, performing the non-sequential parsing process can include performing the non-sequential parsing process to identify one or more data elements. The one or more data elements respectively include the one or more values and one or more field identifiers that identify the one or more fields of the plurality of unique fields. In some implementations, each of the plurality of regular expressions is configured to identify a field identifier and a corresponding value. In some implementations, each of the one or more data elements comprises a GS1-format element string comprising a field identifier and a corresponding value that immediately follows the field identifier in the element string.

In some implementations, the one or more fields include at least one of a lot number, a serial number, a creation date (i.e., a manufacturing date), or a best-by date.

At 308, the computing system can store, for each of the one or more values, a data object that comprises the value and information indicative of the field for the value. For example, the computing system can store the data objects in a data store that is accessible to the computing device via the API. In some implementations, the computing system can transmit, via the API, the one or more data objects to the computing device associated with the cataloguing system.

ADDITIONAL DISCLOSURE

The technology discussed herein makes reference to servers, databases, software applications, and other computer-based systems, as well as actions taken and information sent to and from such systems. The inherent flexibility of computer-based systems allows for a great variety of possible configurations, combinations, and divisions of tasks and functionality between and among components. For instance, processes discussed herein can be implemented using a single device or component or multiple devices or components working in combination. Databases and applications can be implemented on a single system or distributed across multiple systems. Distributed components can operate sequentially or in parallel.

While the present subject matter has been described in detail with respect to various specific example embodiments thereof, each example is provided by way of explanation, not limitation of the disclosure. Those skilled in the art, upon attaining an understanding of the foregoing, can readily produce alterations to, variations of, and equivalents to such embodiments. Accordingly, the subject disclosure does not preclude inclusion of such modifications, variations and/or additions to the present subject matter as would be readily apparent to one of ordinary skill in the art. For instance, features illustrated or described as part of one embodiment can be used with another embodiment to yield a still further embodiment. Thus, it is intended that the present disclosure cover such alterations, variations, and equivalents.

What is claimed is:
1. A computing system, comprising:
one or more processors; and
one or more non-transitory computer-readable media that store instructions that, when executed by the one or more processors, cause the one or more processors to perform operations, the operations comprising:

receiving, via an application programming interface (API), object information from a requesting computing device, wherein the object information is:
(a) extracted from a machine-readable code associated with the object; or
(b) derived from information extracted from the machine-readable code associated with the object;

performing, via a non-sequential parsing module, a non-sequential parsing process to the object information to identify one or more data elements comprising one or more values and one or more field identifiers for one or more fields of a plurality of unique fields, wherein the one or more field identifiers comprise one or more encoded values that identify the one or more fields, and wherein performing the non-sequential parsing process comprises:

applying, via the non-sequential parsing module, a plurality of regular expressions to the object information to identify the one or more values, wherein each of the plurality of regular expressions is configured to identify values for at least one field of the plurality of unique fields, wherein applying the plurality of regular expressions to the object information comprises:

applying a first regular expression to the encoded sequence of values to identify a first value of a first field from a first segment of the encoded sequence of values, wherein the first regular expression is configured to identify values for the first field; and applying a second regular expression to the encoded sequence of values to identify a second value of a second field from a second segment of the encoded sequence of values, wherein the second regular expression is configured to identify values for the second field, and wherein the second segment occurs prior to the first segment within the encoded sequence of values; and in response to identifying the one or more data elements, storing, for each of the one or more values, a data object that comprises the value and information indicative of the field for the value.

2. The computing system of claim 1, wherein the operations further comprise transmitting, via the API, each data object to the requesting computing device.

3. The computing system of claim 1, wherein the machine-readable code comprises a barcode.

4. The computing system of claim 3, wherein the barcode comprises a two-dimensional barcode.

5. The computing system of claim 3, wherein the barcode comprises a Health Industry Bar Code (HIBC).

6. The computing system of claim 1, wherein the machine-readable code comprises a QR code.

7. The computing system of claim 1, wherein each of the plurality of regular expressions is configured to identify a field identifier and a corresponding value.

8. The computing system of claim 6, wherein each of the one or more data elements comprises a GS1-format element string comprising a field identifier and a corresponding value that immediately follows the field identifier in the element string.

9. The computing system of claim 1, wherein receiving the object information from the requesting computing device comprises receiving, via the API, an encoded sequence of values that is extracted from the machine-readable code associated with the object.

10. The computing system of claim 1, wherein the object comprises a medical resource or medical device, and wherein the computing system and/or the requesting computing device is associated with a medical cataloguing system.

11. The computing system of claim 1, wherein the one or more fields comprise at least one of:
a lot number;
a serial number;
a creation date; or
a best-by date.

12. The computing system of claim 1, wherein receiving the object information from the requesting computing device comprises:
receiving, from the requesting computing device associated via the API, a sequence of binary values extracted from the machine-readable code associated with the object; and
deriving the object information from the sequence of binary values.

13. A computer-implemented method, comprising:
receiving, by a computing system comprising one or more processor devices via an application programming interface (API), object information from a requesting computing device, wherein the object information is:
(a) extracted from a machine-readable code associated with the object; or
(b) derived from information extracted from the machine-readable code associated with the object;
performing, by the computing system, a non-sequential parsing process to the object information to identify one or more data elements comprising one or more values and one or more field identifiers for one or more fields of a plurality of unique fields, wherein the one or more field identifiers comprise one or more encoded values that identify the one or more fields, and wherein performing the non-sequential parsing process comprises:
applying, by the computing system, a plurality of regular expressions to the object information to identify the one or more values, wherein each of the plurality of regular expressions is configured to identify values for at least one field of the plurality of unique fields, wherein applying the plurality of regular expressions to the object information comprises:
applying a first regular expression to the encoded sequence of values to identify a first value of a first field from a first segment of the encoded sequence of values, wherein the first regular expression is configured to identify values for the first field; and
applying a second regular expression to the encoded sequence of values to identify a second value of a second field from a second segment of the encoded sequence of values, wherein the second regular expression is configured to identify values for the second field, and wherein the second segment occurs prior to the first segment within the encoded sequence of values; and
storing, by the computing system for each of the one or more values, a data object that comprises the value and information indicative of the field for the value.

14. The computer-implemented method of claim 13, wherein the method further comprises transmitting, by the computing system via the API, each data object to the requesting computing device.

15. The computer-implemented method of claim 13, wherein each of the plurality of regular expressions is configured to identify a field identifier and a corresponding value.

16. The computer-implemented method of claim 15, wherein each of the one or more data elements comprises a GS1-format element string comprising a field identifier and a corresponding value that immediately follows the field identifier in the element string.

17. One or more non-transitory computer-readable media that store instructions that, when executed by one or more processors of a computing system, cause the one or more processors to perform operations, the operations comprising:

receiving, via an application programming interface (API), object information from a requesting computing device, wherein the object information is:

(a) extracted from a machine-readable code associated with the object; or (b) derived from information extracted from the machine-readable code associated with the object;

performing a non-sequential parsing process to the object information to identify one or more data elements comprising one or more values and one or more field identifiers for one or more fields of a plurality of unique fields, wherein the one or more field identifiers comprise one or more encoded values that identify the one or more fields, and wherein performing the non-sequential parsing process comprises:

applying a plurality of regular expressions to the object information to identify the one or more values, wherein each of the plurality of regular expressions is configured to identify values for at least one field of the plurality of unique fields, wherein applying the plurality of regular expressions to the object information comprises:

applying a first regular expression to the encoded sequence of values to identify a first value of a first field from a first segment of the encoded sequence of values, wherein the first regular expression is configured to identify values for the first field; and applying a second regular expression to the encoded sequence of values to identify a second value of a second field from a second segment of the encoded sequence of values, wherein the second regular expression is configured to identify values for the second field, and wherein the second segment occurs prior to the first segment within the encoded sequence of values; and storing, for each of the one or more values, a data object that comprises the value and information indicative of the field for the value.

\* \* \* \* \*